United States Patent [19]

Pittman, Jr. et al.

[11] 4,258,206

[45] Mar. 24, 1981

[54] SELECTIVE CARBONYLATION OF OLEFINS BY A POLYMER-SUPPORTED PD HALIDE CATALYST

[75] Inventors: Charles U. Pittman, Jr., Tuscaloosa, Ala.; Quock Y. Ng, Lake Elmo, Minn.

[73] Assignee: The University of Alabama, University, Ala.

[21] Appl. No.: 57,819

[22] Filed: Jul. 16, 1979

Related U.S. Application Data

[62] Division of Ser. No. 941,077, Sep. 11, 1978, abandoned.

[51] Int. Cl.³ .................... C07C 67/38; C07C 51/14
[52] U.S. Cl. ........................ 560/233; 260/410.9 R; 252/431 P; 562/522
[58] Field of Search ............... 560/233; 260/410.9 R; 562/522

[56] References Cited

U.S. PATENT DOCUMENTS

| | | | |
|---|---|---|---|
| 3,501,518 | 3/1970 | Kutepow | 560/233 |
| 3,641,074 | 2/1972 | Fenton | 560/233 |
| 3,668,249 | 6/1972 | Fenton | 560/233 |
| 3,700,706 | 10/1972 | Butter | 560/233 |
| 3,793,369 | 2/1974 | Hara | 560/233 |
| 3,864,372 | 2/1975 | Svoboda | 252/431 P |
| 3,865,853 | 2/1975 | Hinze | 252/429 R |
| 3,887,595 | 6/1975 | Nozaki | 560/233 |
| 3,931,123 | 1/1976 | Vacik | 252/429 R |
| 3,987,009 | 10/1976 | Young | 252/429 R |

OTHER PUBLICATIONS

Evans, J. Organomet. Chem., 67, pp. 295–314, (1974).
Pittman, J. Am. Chem. Soc., 97, pp. 1742–1748, 1749–1754, (1975).
Pittman, J. Am. Chem. Soc., 98, pp. 5402–5405, (1976).
Pittman, J. Organomet. Chem., 153, pp. 85–97, (1978).
Basolo, "Catalysis Progress in Research", pp. 177–185, (Plenum Press, 1973).
Pittman, "Organic Synthesis with Polymer-Attached Homogeneous Catalysts", 295, pp. 15–35, (1977).

*Primary Examiner*—Natalie Trousof
*Assistant Examiner*—Michael Shippen
*Attorney, Agent, or Firm*—Oblon, Fisher, Spivak, McClelland & Maier

[57] ABSTRACT

A solid supported catalyst useful in the carbonylation of olefins represented by the formula

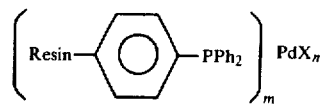

wherein Resin- represents a cross-linked solvent swellable high molecular weight resin; X represents a halide; m+n=4. A method for the carbonylation of α-olefins using the above-mentioned solid-supported catalyst.

24 Claims, 10 Drawing Figures

SELECTIVE CARBONYLATION OF OLEFINS BY A POLYMER-SUPPORTED PD HALIDE CATALYST

This is a division of application Ser. No. 941,077, filed Sept. 11, 1978, now abandoned.

BACKGROUND OF THE INVENTION

1. Field of the Invention

This invention relates to a method for the carbonylation of α-olefins by alcohols, water or mixture thereof and CO in the presence of a solid-supported Pd halide catalyst.

2. Description of the Prior Art

Alkoxycarbonylation is the addition of carbon monoxide to unsaturated compounds in the presence of alcohols to give carboxylic esters. It may be catalyzed by a variety of metal carbonyls in homogeneous solution. Alkoxycarbonylation of α-olefin catalyzed by nickel and cobalt carbonyls (Reppe type catalysts) is characterized by the production of large amounts of branched (b), as well as, minor amounts of the linear (n) acid derivatives (Reppe, J. Liebig Ann. Chem., 582, 1 (1953)); (equation 1).

$$RCH=CH_2 + CO + R'OH \longrightarrow \underset{\underset{CH_3}{|}}{RCHCO_2R'} + RCH_2CH_2COOR' \quad (1)$$
$$\qquad\qquad\qquad\qquad\qquad (b) \qquad\qquad (n)$$

These Reppe reactions require vigorous conditions. For example, high temperatures and pressures (250°–320° and 200–300 atm) are needed in the carbonylation of olefins (ethylene, propylene). However, using temperatures above 150° often leads to side reactions, such as the water-gas shift reaction (equation 2). The resulting hydrogen reduces the unreacted olefin, and $$CO + H_2O \rightarrow CO_2 + H_2 \quad (2)$$

promotes olefin hydroformylation to aldehydes, alcohols and ketones. Other complications include isomerization and polymerization of the olefin and increased corrosion of process equipment.

Palladium complexes, of the general formula $L_mPdZ_n$, are active catalysts for the carbonylation of olefins at low temperatures (<120°) (Bittler et al, Angew. Chem. Int. 7, 329 (1968)). $L_m$ denotes a ligand such as phosphine, nitrile, amine or olefin; Z is a halide or an acid anion, and m+n is 3 or 4. Among the active catalysts reported by Bittler are $(Ph_3P)_2PdCl_2$, $(C_5H_{11}N)$—$PdCl_2(PPh_3)$, and $(PhCH_2NH_2)PdCl_2(PPh_3)$. However, in these reactions, the principal product is still mostly the branched ester.

Recent studies have shown that the straight-chain isomer can be made the predominant product by addition of basic and bulky ligands to Bittler's catalysts. The main factor in the formation of the straight-chain ester appears to be steric. It is possible to hypothesize the formation of two intermediate σ-complexes between Pd(II), alcohol (R'OH), stabilizing ligand L and olefin (R—CH=CH$_2$) (1 versus 2):

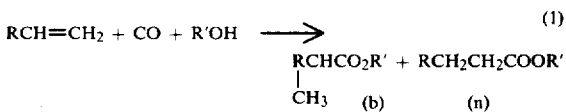

These two σ-complexes differ by the mode of attachment of the olefin to the Pd atom. In case 1 the attachment occurs through the secondary carbon atom, while in case 2 the attachment is through the primary carbon. The σ-complex 1, which leads to branched product, is more sterically crowded than the σ-complex 2 leading to the normal product.

Fenton (J. Org. Chemistry, 38, 3192 (1973)), has pointed out that in the absence of mineral acid, the steric environment of the metal atom is the crucial factor in determining whether a normal or branched product would be formed. In the presence of mineral acid protonation of the olefin is Markovnikov. Therefore, the resulting alkyl cations form the alkyl-palladium complexes at the more substituted carbon atom (1). Thus, in the presence of mineral acid, the product would be mainly the branched carboxyl compound.

Recently, Knifton (J. Org. Chemistry, 41, 793, 2888 (1976) and U.S. Pat. No. 3,819,669) has shown that $(Ph_3P)_2PdCl_2$-$SnCl_2$ (1:10) is an active catalyst for the alkoxycarbonylation of 1-heptene. At 70 percent conversion 89 percent of the product is linear ester (equation 3).

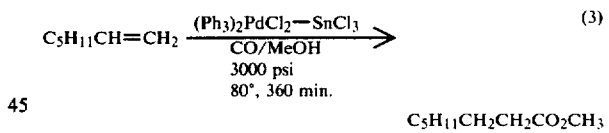

Carbonylation of 1-heptane in methanol-$d_1$ yield methyl octanoate-3-$d_1$ (equation 4).

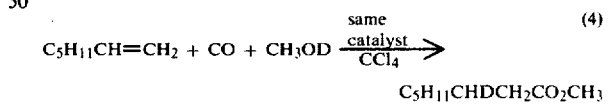

It is reasoned by Knifton that the anti-Markovnikov H addition is favored because the bulkiness of $SnCl_3^-$ and $Ph_3P$ ligands would force the α-olefin to approach the metal with its less crowded α-carbon. The linear ester is highly favored and is observed as the major product. This higher selectivity could result from the fact that complex 3 (see below) is less sterically crowded than the corresponding complex 4. Thus, CO insertion into the C-Pd bond of 3 would be favored over CO insertion into the same bond in 4.

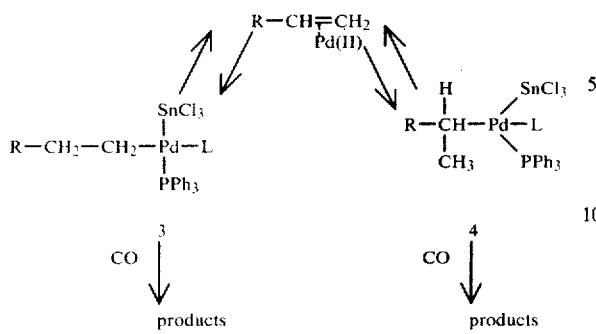

Knifton's studies represent the highest linear ester selectivity reported for α-olefin alkoxycarbonylation (n/b, 9-10:1).

Isomerization of α-olefins to internal olefins is also an important consideration in alkoxycarbonylation. It can be a serious problem when normal carbonylation products are desired. Wells et al (J. Chem. Soc. 1514, 1521 (1973)) have observed that the isomerization of 1-pentene to 2-pentene is catalyzed by both PtH(SnCl$_3$)(Ph$_3$P)$_2$ and PdCl$_2$(PhCN)$_2$ in benzene. The main isomerization product for the Pt complex was cis-2-pentene.

Trans-2-pentene was the main product when PdCl$_2$—(PhCN)$_2$ was the catalyst. It is obvious that isomerization of an α-olefin to an internal olefin would be a serious problem if the rate of this process was competitive with alkoxycarbonylation. Furthermore, the presence of larger amounts of internal olefin in the reaction would reduce the rate of terminal alkoxycarbonylation.

The methods in the above cited references depend on the use of homogeneous Pd-containing catalysts for the alkoxycarbonylation of olefins. It would be useful, from an industrial standpoint to carry out similar reactions using a polymer-supported system. Homogeneous organometallic catalysts cannot be as easily recovered and reused as polymeric systems. Polymer-supported catalysts are advantageous in that they can be easily separated from the reaction mixture by filtration and can be repeatedly used in subsequent reactions. However, it is very important industrially to achieve a high n/b ratio (linear selectivity) and minimize isomerization reactions during alkoxycarbonylation since otherwise the process becomes uninteresting economically and introduces at least two or more extra separation and purification steps. There are, in addition, some potential problems which don't always render obvious the transition from homogeneous to heterogeneous systems. These distinctions between homogeneous and heterogeneous catalysis may be due to a variety of factors. Where reactants must diffuse into a swollen polymer matrix to reach the bound catalytic site, reaction rates may be lowered because diffusion becomes a late limiting effect.

Another related factor is that the concentration of reactants at the catalytic site can be different for polymer-bound systems than it is when the catalyst is simply dissolved in solution. Also there are differences in solvation energies between the bulk solution and the inside of the swollen polymer matrix.

Finally, the interaction between the polymer support and the active catalytic species itself, sometimes forces changes in the nature and composition of the anchored catalyst, so as to make the composition different from what it is in homogeneous media.

Pittman (J. Amer. Chem. Society, 97, 1742 (1975)) has prepared a diphenylphosphine-substituted polystyrene resin which appeared potentially useful for the preparation of palladium halide-containing catalysts and their use in the alkoxycarbonylation of olefins. Furthermore, Pittman (J. Organometallic Chem., 153, 85 (1978) prepared similar resins, to which palladium in the formal zero valence state was attached, and these resins were employed to catalyze the dimerization-methoxylation of butadiene. Industrially, esters are used in explosives, plastics, photographic films, lacquers, rayon, paints, varnishes, and soaps and as intermediates. Several esters are high tonnage chemicals, total production in the U.S. alone, running in excess of 300 million lb annually. Carboxylic acids also play an important role in various organic synthesis, including those required for the manufacture of plastics, elastomers and various other synthetic materials. It is thus important to develop new and ever more efficient industrial methods for the synthesis of these useful materials.

SUMMARY OF THE INVENTION

It is therefore an object of this invention to provide a method for the synthesis of carboxylic acids and esters.

It is also an object of the invention to provide a method for the synthesis of acids and esters by carbonylation of olefins. It is another object of the invention to provide a method for the carbonylation of olefins with a large selectivity towards the linear isomer over the branched isomer. An additional object of the invention is to provide a method for the carbonylation of olefins which will take place with a minimum amount of isomerization of the starting olefin. A further object of the invention is to provide a method for the carbonylation of olefins using a polymer-supported insoluble catalyst.

Still another object of the invention is to provide a polymer-supported catalyst for the carbonylation of olefins. A still further object of the invention is to provide a polymer-supported Pd(II) halide catalyst useful in the carbonylation of olefins which will give a high n/b selectivity in the reaction.

These and other objects of the invention as will hereinafter become readily apparent have been achieved by providing a method for the carbonylation of α-olefins which comprises reacting at 70°–200° C. an olefin with carbon monoxide at a pressure of 100–2500 psi, with a primary alcohol or water, or a mixture thereof, and with a catalyst represented by the formula:

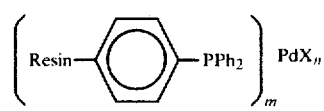

wherein Resin- represents a cross-linked swollen high molecular weight resin with permeatable micropores and wherein said α-olefin and said alcohol or water are capable of permeating the micropores of said swollen resin.

These objects have also been achieved by providing a catalyst useful in the carbonylation of olefins which comprises a polymer represented by the formula $$\left( \text{Resin} - \underset{m}{\bigcirc} - \text{PPh}_2 \right) \text{PdX}_n$$

wherein Resin- represents a crosslinked, solvent-swellable, high molecular weight resin; m+n=4; X is a halide.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
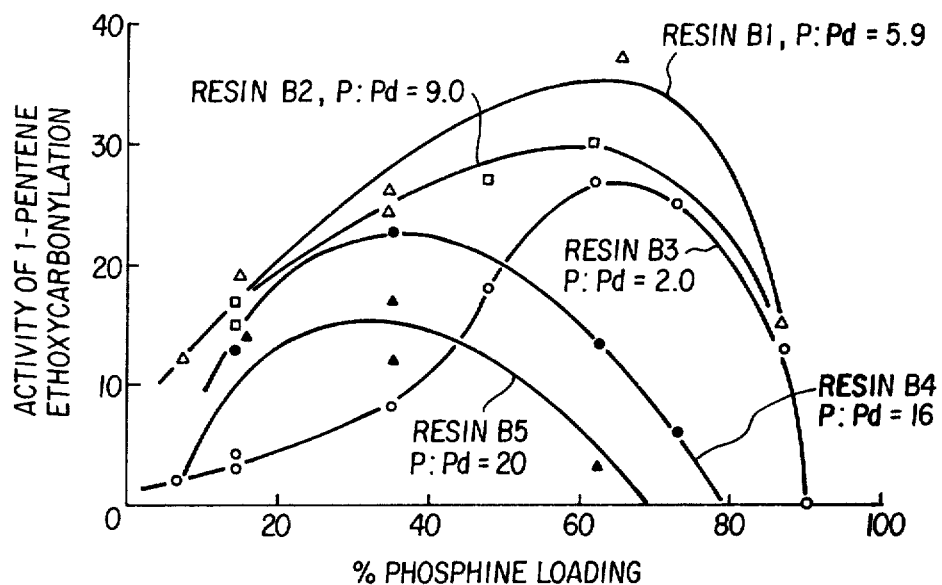
FIG. 1 describes the effects of % phosphine loading on the activity of the palladium halide anchored polymer.

Improved selectivity for linear esters is achieved with polymer-attached catalysts over their homogeneous counterparts. For example, the normal to branched ratio (n/b) is 17 (94 percent) for the attached catalyst of the present invention versus 4 (80 percent) for a homogeneous catalyst, under similar reaction conditions. ([Pd]=5×10⁻³ M, P:Pd=32, 400 psi CO, 120°). This higher n/b selectivity exhibited by the anchored catalysts does not appear to be a concentration effect, since it remains higher than that obtainable with homogeneous catalysts at equal palladium and phosphine concentrations. For example, a resin catalyst with phosphine loading (PL)=63.7 percent, (true concentration of Pd in the resin: [Pd]=50×10⁻³ M) showed a n/b=12, versus 6 with a homogeneous catalyst ([Pd]=50×10⁻³ M), both catalysts at P:Pd=20 (400 psi CO, 120°).

The complete reaction system includes an α-olefin, a polymer-anchored catalyst containing Pd halide, a primary alcohol or water, or mixture thereof and carbon monoxide.

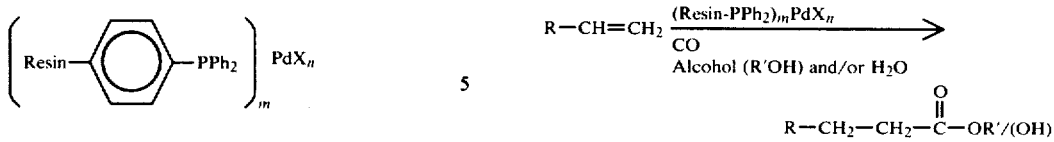

$$R-CH_2-CH_2-\overset{O}{\overset{\|}{C}}-OR'/(OH)$$

wherein m+n=4; X=halide.

Polymer resins useful in the anchoring of the catalysts include any lightly crosslinked matrix which is swellable by solvents. The amount of crosslinking is defined by two factors. The lower limit has to be high enough so as to prevent solubilization of the resin in the solvent, i.e., make the resin insoluble. The upper limit has to be low enough so as to prevent the resin from becoming too rigid, i.e., it has to maintain chain flexibility. Preferred limits are 0.5-4%, most preferred is 1-2%. Among these resins is 1% Divinyl Benzene (DVB)-polystyrene beads (obtained from BioRad Laboratories with trade name BioBeads SX-1). This resin is easily swellable by ethers such as diethyl ether, diisopropyl ether, THF; by aliphatic hydrocarbons, such as pentane, hexanes, cyclohexane, cyclopentane, isopentane; by aromatic hydrocarbons such as benzene, toluene, xylene; by halogenated hydrocarbons such as carbon tetrachloride, chloroform, methylene chloride, chlorobenzene, dichloroethane, tetrachloroethane; by ethyl acetate, acetonitrile and other similar solvents, and mixtures thereof.

Aliphatic hydrocarbon solvents are poor resin swellers. However since the resin does not have to be too swollen to work, they can still be used. It is of course, possible to mix such solvents with other, more efficient swelling solvents. Other resins useful for the present invention, include 2% or 3% DVB-styrene beads, (organic solvent swellable); copolymers of styrene/DVB (4 to 60%) of the macroreticular type, styrene/DVB hydroxyethylmethacrylate (to 50%) terpolymers which are water and alcohol swellable; polystyrene grafted with polyethylene glycol polymer (alcohol swellable). Many other polymer matrices may be used including poly(methyl methacrylate)-hydroxyethyl methacrylate copolymers crosslinked with bisacrylate, lightly crosslinked polyphenylene oxides, lightly crosslinked styrene-butadiene and styrene-α-olefin copolymers and terpolymers, and lightly crosslinked polyesters and polyamides. It is understood that for each class of polymers, attached —PPh₂ groups or —OP(OR)₂ groups are present along the polymer. Poly(vinyl chloride) type polymers are unsatisfactory because they degrade. Preferred resins are organic solvent swellable ones, such as the DVB-polystyrene resins; most preferred is 1%-2% DVB-polystyrene beads. The bead size is preferably 200-400 mesh.

The transformation of the unsubstituted polymer backbone to yield the phosphine-containing resin is carried out following the method of Pittman et al. (J. Amer. Chem. Soc. 97, 1742, (1975)). The resin is first brominated on the aromatic rings to yield the bromo-substituted polyaromatic polymers. These intermediates are then treated with LiPPh₂ to produce diphenylphosphine-substituted polyaromatic polymers. Finally, the phosphinated resin is preferably treated with (PhCN)₂PdX₂ (X=halide) to yield the polymer-anchored catalyst of the present invention. The final reaction is generally carried out with liganded PdX₂ compounds such as L₂PdX₂, wherein L is a neutral electron pair-donating, stabilizing ligand. Examples of such ligands are amines, diamines, nitriles, dinitriles, phosphines, diphosphines. Preferred are phosphines and nitriles. Most preferred is PhCN. Inert non-interferring, organic solvents are used, such as ethers, hydrocarbons and halogenated hydrocarbons. The temperatures for this last reaction range from room temperature to the refluxing temperature of the solvent. Preferred temperatures are 40°–300° C., most preferred are 40°–200° C., (Scheme I).

Scheme I:

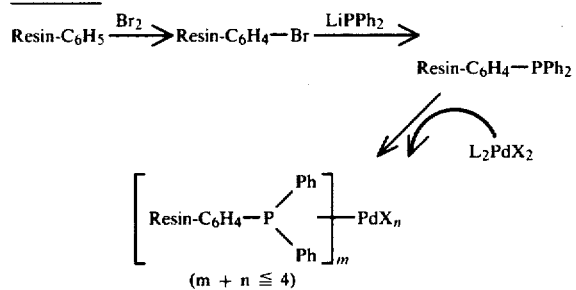

X is a halide selected from the group consisting of F, Cl, Br and I. Preferred is Cl, Br, I.

The olefins which can be alkoxycarbonylated by the method of the present invention include any α-olefin which is capable of permeating into the micropores of the polymer. It is well known that large molecules such as polystyrene of MW 14,000 are capable of permeating the BioBeads SX-1. It can therefore be concluded that the range of useful α-olefins is extensive. Preferred are α-olefins containing 2 to 30 carbon atoms, more preferably 2–18 carbon atoms.

As mentioned above, any solvent capable of swelling the resin is useful in the present methodology. The nature of the resin and the particular carbonylation reaction will of course determine what solvent is preferred. When only alkoxycarbonylation reaction is desired, the solvent should be capable of dissolving all reactants except the resin, it should be non-reactive with the catalytic system and should not interfere with the alkoxycarbonylation reaction, i.e., an inert solvent. However, when both alkoxy- and hydroxy-carbonylation reactions are desired, the solvent may contain water. One of the products of the reaction will then be the carboxylic acid derived from the olefin, rather than only the corresponding ester. When using aqueous tetrahydrofuran as the solvent, for example, in the presence of alcohols, a fraction of the product will be carboxylic acid, and a fraction will be the ester. If hydroxycarbonylation reaction is desired, the solvent will, of course, be pure water or a mixture of a water-miscible inert solvent (not an alcohol) and water. The resin in this case has to be water swellable.

When alkoxycarbonylation is carried out in an alcohol as solvent, it can be the same alcohol that is used to make the ester, of course. The resin in this case has to be alcohol swellable for optimum rates.

Primary alcohols capable of permeating the resin can generally be used in the present method. Preferred are alcohols containing 1 to 30 carbon atoms. Most suitable alcohols have 1–15 carbon atoms. Primary polyols such as ethylene glycol, diethylene glycol, glycerol, 4-hydroxy-n-butanol and similar other ones can also be used. The resulting products obtained therefrom will of course be diesters.

In alkoxycarbonylation reaction, the molar ratio of alcohol to olefin is at least 1:1, but preferably, an excess of alcohol over olefin should be used. This excess can be preferably between 10:1 to 100:1, but the upper limit of alcohol concentration is only defined by the effect of alcohol on the swellability of the resin used. Large absolute concentrations of alcohol decrease the swellability of certain resins. With alcohol-swellable resins, this problem is, of course, overcome. The upper limit in the absolute concentration of the olefin is also given by the effect of olefin on resin swellability. The concentration of Pd *within the swollen resin* is the same no matter how much resin is charged to the reactor. Thus, one does not discuss the concentration of Pd (as in a homogeneous reaction) but rather the mmol. of Pd added to a given reaction solution volume or the mmol. of Pd added per mmol. of olefin. The amount of resin added to the reaction mixture is computed on the basis of the effective molar amount of Pd present versus the amount of olefin added. It will be given hereinafter as the ratio mmol. of olefin/mmol. of Pd charged to the reactor vessel. This ratio can be in the range 5000 to 20, preferably 600 to 100 in batch runs. The time of reaction will depend on temperature, the nature of solvent and on the moisture of the resin. It can be readily determined by one skilled in the art.

Effect of Group IV-B Ligands

It is quite unexpected and surprising tha the polymer-anchored catalysts of the present invention give very high selectivity (n/b ratio) without the addition of $SnCl_2$ or other Group IV-B ligands to the Pd(II) species. This characteristic of the present catalysts is unexpected since, in view of Knifton's work (J. Org. Chem., 41, 2885 (1976)) it has been assumed that high n/b selectivity can be obtained only in the presence of $SnCl_2$. In fact, upon comparing the effect of Group IV-B ligands on homogeneous and on polymer-supported catalysts, it was found that the results are strikingly opposed. Addition of Group IV-B ligands to the polymer-supported catalysts decrease their selectivity while lack of $SnCl_2$ in the polymer catalysts increase selectivity. Table 1 shows the effect of added Sn(II) chloride on the activity and selectivity in alkoxycarbonylation of 1-pentene.

The table shows that the n/b selectivity drops by a factor of five on addition of tin(II) chloride to polymer attached catalyst. For example, run 1, with 47.6 percent Pd and P:Pd=8, shows a drop in its n/b ratio from 16.5 to 3.1 when 10 moles $SnCl_2$ per mole of palladium are added. The activity of the attached catalysts is lowered only slightly, again in contrast to the homogeneous systems.

Fenton (J. Org. Chem, 38, 3192 (1973)) has shown that values of n/b of 2 to 6 can be obtained with homogeneous Pd(II) catalysts without addition of $SnCl_2$. Knifton has improved on this work by obtaining values of n/b of 7 to 10 with addition of a 10-fold excess of $SnCl_2$ or other Group IV-B metals. (J. Org. Chem. Soc., 41, 2885 (1976)). The present invention, on the other hand, gets even higher values of n/b (12–17) that previously obtained, and does so without addition of Group IV-B metals.

It appears that the interaction of polymer with catalytic species is able to replace for the effect of Group IV-B ligands and even improve on it. In fact, Group IV-B ligands act as a poison to the polymer-anchored catalyst. When 1-pentene was alkoxycarbonylated the isomerization product, 2-pentene, was detected only at low CO pressures (≦200 psi, 120° C.) indicating that the side reaction is suppresed in the polymer-bound catalysts.

TABLE 1
EFFECT OF ADDED TIN(II) CHLORIDE ON THE ACTIVITY AND SELECTIVITY IN ALKOXYCARBONYLATIONS OF 1-PENTENE. COMPARISON OF HOMOGENEOUS CATALYSTS WITH THEIR POLYMER-ATTACHED ANALOGS

| Run | Catalyst System | Composition P/Pd | Composition Sn/Pd | 1-Pentene Conversion (mol. %) | Selectivity n/b |
|---|---|---|---|---|---|
| 1 | Resin-$(PPh_2)_xPdCl_y$ PL = 47.6% | 8 | | 26 | 16.5 |
| 2 | Resin-$(PPh_2)_xPdCl_y$-$10SnCl_2$ PL = 47.6% | 8 | 10 | 22 | 3.1 |
| 3 | Resin-$(PPh_2)_xPdCl_y$ PL = 47.6% | 3 | | 18 | 8.9 |
| 4 | Resin-$(PPh_2)_xPdCl_y$-$3SnCl_2$ PL = 47.6% | 3 | 3 | 17 | 1.6 |
| 5 | $(Ph_3P)_2PdCl_2$ | 2 | | 49 | 1.9 |
| 6 | $(Ph_3P)_2PdCl_2$-$11SnCl_2$ | 2 | 11 | 22 | 8.7 |
| 7 | $(Ph_3P)_2PdCl_2$-$7PPh_3$ | 9 | | 47 | 5.2 |
| 8 | $(Ph_3P)_2PdCl_2$-$8PPh_3$-$10SnCl_2$ | 10 | 10 | 48 | 4.4 |

Effect of Phosphine Loading and P:Pd Ratio

For the polymer-attached catalysts, activity is dependent on the extent of phosphine loading (PL, the percent of resin repeating units which have been substituted by the diphenylphosphide group) and on the phosphine to palladium (P:Pd) ratios. The activities of resin catalysts with low P:Pd ratios approach maxima at high phosphine loadings while resin catalysts with high P:Pd ratios exhibit activity maxima at low PL. Resin catalysts with high P:Pd and PL tend to give high n/b ratios.

The alkoxy- and hydroxycarbonylation reactions can be carried out with phosphine loadings in the range of 0.5–99.5% and with P:Pd ratios of 1–99. The swellability of the polymers, once again, presents a limit to the upper values of the PL and the P:Pd ratio. At high PL's the swellability of the polymer decreases and at any given PL value, the upper Pd value will also depend on the swellability of the polymer. In all instances, if the polymer becomes less swellable, its permeability decreases and diffusion of reactants into the polymer becomes hindered.

Although the broad ranges for PL and P:Pd mentioned above are useful in the present invention, a preferred range for PL is 20–80% and for P:Pd is 2–60. Most preferred ranges are 40–70% and 5–25 respectively. With certain combination of values, maxima in activity can be reached, for example, at 60–63% PL and P:Pd=2.0. However, a maximum in n/b for a P:Pd of 2 can be reached with a PL in the range of 30–80%. It will be clear then that combinations that yield a maximum in activity will not always correspond to combination that yield a maximum in selectivity. In many instances, compromise values have to be reached that will maximize both yield and selectivity simultaneously. Values of 48% PL and P:Pd=6 represent such a compromise, but other such combinations can easily be found by one skilled in the art. Referral to tables and Figures in the Examples section will also aid in finding these compromise values.

In the heterogeneous system, at high PL, the phosphine concentration in a given volume fraction of the polymer is high. This coupled with the segmental mobility of the polymeric ligand, increases the microscopic concentration of available ligand to a given metal atom, at constant macroscopic P:Pd ratios. It appears that special frequency factors exist for P collisions with Pd which do not exist in a homogeneous solution. This could be called a polymer "proximity effect." The overall mobility of anchored phosphine sites, however, it ultimately limited by crosslinking of the polymer's matrix. This in turn would suppress the palladium dimerization tendency (a problem in homogeneous systems). The degree of coordinative unsaturation of a given Pd atom may be reduced by the high values of PL. At low P:Pd ratios more coordinatively unsaturated palladium species can form via dissociation processes.

The availability of the phosphine ligands to a palladium atom (P:Pd ratio) may affect the rate of the reaction and product selectivity. The former may be affected through the ligand dissociation process to produce the catalytically active complexes, and through the ligand's contribution to the Lewis basicity of the metal. Product selectivity may also be influenced by the steric bulkiness of the ligands. Bulky ligands, such as triphenylphosphine, would force the approach of an α-olefin to a metal atom by its terminal carbon more than by an internal carbon. Ultimately this would lead to the normal product.

Effects of Pressure and Temperature

The pressure of CO useful in the present invention is in the range 25–2500 psi, the preferred range being 100–1200 psi and the most preferred 400–800 psi. This pressure of CO can be obtained by using pure CO gas or by using a mixture of CO and an inert gas at a partial pressure of CO having the value set forth above.

The behavior of homogeneous and polymer-supported catalysts is different as a function of pressure.

The activity of a typical homogeneous catalyst generally decreases with increased CO pressures, while the reactivities for the resins increase with CO pressure to a maximum and then decrease.

The lower limit of temperature will depend on the desired rate of reaction and the upper limit will depend on the amount of decomposition which can be tolerated. Generally, these limits are between 70°–200° C., preferably 100°–180° C., most preferably 115°–150° C.

The resin catalysts are found to maintain catalytic activities at higher temperatures than a homogeneous catalyst, remaining catalytically active even at 180°, while homogeneous catalysts show a sharp decrease in activity after 140°. At all temperatures and CO pressures the resin catalysts are more selective than their homogeneous counterparts. The selectivity of the polymer-supported catalysts tend to decrease at higher temperatures while still remaining higher than the homogeneous catalysts.

The present invention leads to the conclusion that resin-anchored catalysts may be used to give improved n/b selectivities (ca. 94%) when cross-linked solvent-swellable resins are employed. Furthermore, these same resins may be used at higher temperatures, they can be recycled and they can be more easily separated from the reaction than their homogeneous analogues.

Having now described the invention, a further understanding can be obtained by reference to certain specific examples which are provided herein for purposes of illustration only and are not intended to be limiting unless otherwise specified.

A. Preparation of Polymer

Example 1. Bromination of Styrene-divinylbenzene Copolymer

In a typical preparation, cross-linked styrene-one percent divinylbenzene beads (Bio-Beads, SX-1, 200–400 mesh) were cooled in an ice bath and shielded from light. The contents were vigorously stirred and 0.5 gm of iron powder was added. Bromine (9 ml, 0..7 moles) in $CCl_4$ (100 ml) was added dropwise from an addition funnel over a period of 2 hours. The reaction mixture was allowed to warm to room temperature after bromine addition was completed. Generated HBr was swept into an aqueous NaOH trap with a stream of dry nitrogen. The slurry was stirred for 24 hours, solvent removed by filtration on a coarse glass frit funnel, and unreacted iron powder was removed with a magnet. The resin was then washed by stirring successively in one liter each: 5 percent aqueous sodium thiosulfate (one hours), 5 percent aqueous sodium carbonate (one hour), acetone (4–5 hours), benzene/methanol (9:1) (18–24 hours), and methanol (4–5 hours). The beads were vacuum dried (25° C., 0.05 torr) for 24 hours. Bromine analysis showed 35 percent bromine.

Example 2. Preparation of Diphenylphosphine Substituted Copolymer

A THF solution (150 ml) containing chlorodiphenylphosphine (60 g, 0.34 mole) was added dropwise from a dropping flask, and under nitrogen atmosphere to a stirred THF (75 ml) suspension of lithium metal (5 g, 0.7 moles) in a 500 ml round bottom flask. Formation of lithiodiphenylphosphide was indicated by the appearance of a bright red color. After stirring 18 hours, unreacted lithium was removed and the solution was added slowly to a rapidly stirred THF slurry of the brominated resin beads (32 g, 35 percent Br, 131.3 mmol Br). This slurry was allowed to stir two days under nitrogen (longer if high percent Br content resin used). The slurry was then hydrolyzed by adding it to two liters of nitrogen-saturated acetone/water (3:1) and stirring for one hour. The beads were then filtered and washed by stirring successively in one liter each of the following nitrogen-saturated solvents: water (2 hours), acetone (2 hours), benzene/methanol (9:1) (18–24 hours), and methanol (4–5 hours). The beads were then vacuum dried (80° C., 0.05 torr) for 24 hours, and analyzed for 6.44 percent P which corresponds to 35.0 percent of the polystyryl rings substituted with the diphenylphosphide moiety.

Example 3. Preparation of Resin-containing $PdCl_2$

Phosphinated resin (1.7 g, 6.44 percent P, corresponds to 35 percent of polystyryl rings substituted with the diphenylphosphide group, and 3.53 mmole P), and $(PhCN)_2PdCl_2$ (0.0676 g, 0.176 mmole) were placed in a nitrogen-purged 50 ml round bottom flask, along with THF (20 ml). The resulting slurry was stirred under nitrogen and refluxed for two days to accomplish complete ligand exchange. The resin was then transferred to a Soxhlet extractor and extracted to remove soluble catalyst and ligand. The yellow-gold colored polymer-attached catalyst was then dried under vacuum (25° C., 0.05 torr) for two days. Analysis showed 5.41 percent P and 0.88 percent Pd, corresponds to a P=Pd ratio of 21.0:1.

Examples 4–47

Table 2 gives a list of polymer-attached catalysts prepared as specific examples in similar fashion to that of Example 3.

B. Ethoxycarbonylation Reactions

Example 48. Ethoxycarbonylation of 1-Pentene

Ethoxycarbonylation of 1-pentene was carried out in a 150 cm$^3$ stainless steel pressure bomb. The bomb was dried in a 120° oven overnight before use and flushed with nitrogen while cooling. The appropriate amount of catalyst (0.05 mmoles Pd, polymer-bound or soluble) was added, along with an ethanol: tetrahydrofuran (1:1) solution (10 ml). This solvent mixture contains 0.01 mmole/ml mesitylene which was used as a glc internal standard, and 1-pentene (2 ml, 18.3 mmoles). After the contents were sealed, the reactor was pressurized to 400 psig with carbon monoxide and allowed to equilibrate five minutes, then cooled in liquid nitrogen and vented to atmospheric pressure. This procedure was then repeated twice and the bomb was pressurized to the desired pressure with carbon monoxide. The reactor was than placed in an oil bath pre-equilibrated at the proper temperature and shaken with a wrist-action shaker for the desired reaction time. The reactor was then cooled to room temperature, the gases were vented and the reaction solution was analyzed by quantitative glc. The resin was recovered by filtration and dried under vacuum before being recycled. Products were separated by preparative glc and analyzed by $'$H-nmr infrared spectroscopy and mass spectroscopy.

TABLE 2

EXAMPLES OF POLYMER-ATTACHED $(Ph_3P)_2PdCl_2$ CATALYSTS USED FOR THE CARBONYLATION REACTION

| Example # | Catalyst | Percent P | Percent Pd | P/Pd | Percent PL | Percent DVB |
|---|---|---|---|---|---|---|
| 4 | B1-1 | 8.0 | 5.2 | 5.3 | 83.5 | 1 |
| 5 | B2-2 | 5.7 | 2.8 | 6.8 | 63.7 | 1 |
| 6 | B3-3 | 4.4 | 2.7 | 5.6 | 35.0 | 1 |
| 7 | B4-4 | 3.5 | 2.0 | 5.8 | 15.0 | 1 |
| 8 | B5-5 | | | 6.8 | 6.8 | 1 |
| 9 | B2-1 | 5.4 | 2.2 | 8.6 | 63.7 | 1 |
| 10 | B2-2 | 6.4 | 2.8 | 8.0 | 42.2 | 1 |
| 11 | B2-3 | 7.0 | 2.9 | 8.3 | 47.6 | 1 |
| 12 | B2-4 | 3.3 | 1.2 | 9.7 | 14.0 | 1 |
| 13 | B3-1 | 6.3 | 11.5 | 1.9 | 83.5 | 1 |
| 14 | B3-2 | 5.5 | 7.5 | 2.5 | 47.6 | 1 |
| 15 | B3-3 | 2.9 | 8.4 | 1.2 | 14.0 | 1 |

TABLE 2-continued

EXAMPLES OF POLYMER-ATTACHED
(Ph₃P)₂PdCl₂ CATALYSTS USED FOR
THE CARBONYLATION REACTION

| Example # | Catalyst | Percent P | Percent Pd | P/Pd | Percent PL | Percent DVB |
|---|---|---|---|---|---|---|
| 16 | B3-4 | 1.7 | 2.8 | 2.0 | 6.8 | 1 |
| 17 | B4-1 | 8.4 | 1.7 | 16.6 | 73.4 | 1 |
| 18 | B4-2 | 5.3 | 1.1 | 17.2 | 35.0 | 1 |
| 19 | B4-3 | 3.4 | 0.7 | 16.1 | 63.7 | 1 |
| 20 | B4-4 | 5.7 | 1.4 | 14.0 | 63.7 | 1 |
| 21 | B5-1 | 6.7 | 1.2 | 19.8 | 63.7 | 1 |
| 22 | B5-2 | 5.4 | 0.88 | 21.0 | 35.0 | 1 |
| 23 | B5-3 | 5.6 | 0.88 | 21.8 | 35.0 | 1 |
| 24 | B5-4 | 3.2 | 0.56 | 19.3 | 14.0 | 1 |
| 25 | B5 | 5.9 | 0.98 | 20.6 | 9.2 | 1 |
| 26 | B6-1 | 8.1 | 0.96 | 28.9 | 63.7 | 1 |
| 27 | B6-2 | 6.7 | 1.2 | 19.8 | 63.7 | 1 |
| 28 | B6-3 | 5.7 | 1.4 | 14.0 | 63.7 | 1 |
| 29 | B6-4 | 5.7 | 2.8 | 6.9 | 63.7 | 1 |
| 30 | B6-5 | 5.5 | 9.7 | 2.0 | 63.7 | 1 |
| 31 | B7-1 | 5.6 | 0.88 | 21.8 | 35.0 | 1 |
| 32 | B7-2 | 5.4 | 0.88 | 21.0 | 35.0 | 1 |
| 33 | B7-3 | 5.3 | 1.1 | 17.2 | 35.0 | 1 |
| 34 | B7-4 | 4.7 | 8.3 | 1.9 | 35.0 | 1 |
| 35 | B8-1 | 3.2 | 0.56 | 19.3 | 14.0 | 1 |
| 36 | B8-2 | 3.4 | 0.71 | 16.1 | 14.0 | 1 |
| 37 | B8-3 | 3.2 | 1.08 | 10.2 | 14.0 | 1 |
| 38 | B8-4 | 3.3 | 1.17 | 9.7 | 14.0 | 1 |
| 39 | B8-5 | 2.8 | 2.20 | 4.1 | 14.0 | 1 |
| 40 | B8-6 | 2.9 | 8.43 | 1.2 | 14.0 | 1 |
| 41 | B8-7 | 2.8 | 7.82 | 1.2 | 14.0 | 1 |
| 42 | B9 | 7.0 | 2.9 | 8.3 | 47.6 | 1 |
| 43 | B10 | 8.2 | 7.8 | 3.6 | 73.7 | 1 |
| 44 | B11 | 6.3 | 6.0 | 6.3 | 44.7 | 1 |
| 45 | B12 | 8.0 | 5.2 | 5.3 | 83.5 | 1 |
| 46 | B13 | 3.5 | 2.0 | 5.8 | 15.0 | 1 |
| 47 | B14 | 6.3 | 69.0 | 3.1 | 12.0 | 3 |

Both ir and pnmr spectra for products 1-ethyl-hexanoate and ethyl-2-methylpentanoate are identical to the corresponding spectra of products purchased commercially.

Examples 49-74

1-Pentene (2 ml, 18.3 mmole) was alkoxycarbonylated with ethanol in an ethanol:THF solvent (10 ml, containing 85.7 mmol EtOH) with various resins, where the amount of Pd charged to the reactor = 0.05 mmol, with pressure of CO at 400 psi and at 120° for 24 hours. The influence of PL on selectivity and yield are shown in Table 3 and FIGS. 1 and 2.

TABLE 3

RESULTS OF VARYING PHOSPHINE
LOADING (PL) ON ACTIVITY
AND SELECTIVITY OF POLYMER
ATTACHED CATALYST

| Example | Catalyst | P:Pd | Percent PL | 1-Pentene Conversion (mol %)* | Selectivity (n/b) |
|---|---|---|---|---|---|
| 49 | B1-1 | 5.3 | 83.5 | 15.6 | 12.0 |
| 50 | B1-2 | 6.8 | 63.7 | 37.1 | 10.8 |
| 51 | B1-3 | 5.6 | 35.0 | 26.5 | 11.8 |
| 52 | B1-4 | 5.8 | 15.0 | 19.2 | 6.4 |
| 53 | B1-5 | 6.8 | 6.8 | 13.5 | 1.7 |
| 54 | B1-6 | 4.9 | 35.0 | 24.1 | 10.4 |
| 55 | B2-1 | 8.6 | 63.7 | 30.9 | 11.8 |
| 56 | B2-2 | 8.0 | 42.2 | 24.6 | 10.8 |
| 57 | B2-3 | 8.3 | 47.6 | 26.3 | 15.5 |
| 58 | B2-4 | 9.7 | 14.0 | 14.6 | 10.0 |
| 59 | B2-5 | 8.0 | 83.5 | 0 | |
| 60 | B3-1 | 1.9 | 83.5 | 15.5 | 8.7 |
| 61 | B3-2 | 2.5 | 47.6 | 18.3 | 8.5 |
| 62 | B3-3 | 1.2 | 14.0 | 2.5 | 9.2 |
| 63 | B3-4 | 2.0 | 6.8 | 0.4 | 4.1 |

TABLE 3-continued

RESULTS OF VARYING PHOSPHINE
LOADING (PL) ON ACTIVITY
AND SELECTIVITY OF POLYMER
ATTACHED CATALYST

| Example | Catalyst | P:Pd | Percent PL | 1-Pentene Conversion (mol %)* | Selectivity (n/b) |
|---|---|---|---|---|---|
| 64 | B3-5 | 2.0 | 63.7 | 27.0 | 7.8 |
| 65 | B4-1 | 16.6 | 73.4 | 5.9 | 9.2 |
| 66 | B4-2 | 17.2 | 35.0 | 22.8 | 9.2 |
| 67 | B4-3 | 16.1 | 14.0 | 14.7 | 10.4 |
| 68 | B4-4 | 14.0 | 63.7 | 16.0 | 9.5 |
| 69 | B5-1 | 19.8 | 63.7 | 3.8 | 12.1 |
| 70 | B5-2 | 21.0 | 35.0 | 16.3 | 11.7 |
| 71 | B5-3 | 21.8 | 35.0 | 8.1 | 10.3 |
| 72 | B5-4 | 19.3 | 14.0 | 13.9 | 13.3 |
| 73 | B5-5 | 20.6 | 9.2 | 3.0 | 7.2 |
| 74 | B5-6 | 19.6 | 6.8 | Trace | |

*Mol % 1-pentene conversion to hexanoate was normalized to 0.05 mmoles of Pd.

FIG. 1 shows a family of curves depicting the percent conversion per 0.05 mmol Pd in 24 hours (400 psi CO, 120°) versus the percent phosphine loading (PL) for a series of polymer-attached catalysts at different P:Pd ratios. At P:Pd ratios less than 10, maxima in percent conversion are approached near 63 percent PL. At high P:Pd ratios (16 and 20), the maxima of activity are shifted to lower percent PL (near 40 percent PL for P:Pd = 16, and 25 percent PL for P:Pd = 20). The most active catalyst is the one having P:Pd near 6 and PL near 63 percent.

These findings suggest that at low P:Pd ratios, ligand dissociation favors the dimerization of coordinatively unsaturated (and catalytically active) species. This removal of the active species by dimerization reactions must be retarded, (Equation 5) and it is, by having a higher PL.

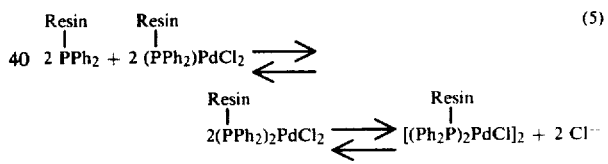

$$2 \text{ PPh}_2^{\text{Resin}} + 2 \text{ (PPh}_2\text{)PdCl}_2 \rightleftharpoons \qquad (5)$$

$$2(\text{PPh}_2)_2\text{PdCl}_2^{\text{Resin}} \rightleftharpoons [(\text{Ph}_2\text{P})_2\text{PdCl}]_2^{\text{Resin}} + 2 \text{ Cl}^-$$

In homogeneous solution, in contrast, catalyst degradative reactions, either in the form of metallic palladium deposition or catalyst dimerization, occur even in the region of low catalyst concentration when the P:Pd ratio is low. To avoid these degradative reactions, a higher P:Pd ratio is usually needed to solubilize the palladium in solution. However, as the phosphine concentration relative to palladium increases fewer coordinatively unsaturated species are formed and the rate decreases thereafter. The best balance between the opposing dimerization and ligand dissociation process, at low P:Pd ratios, appears to be at the high PL region.

Figure 2:
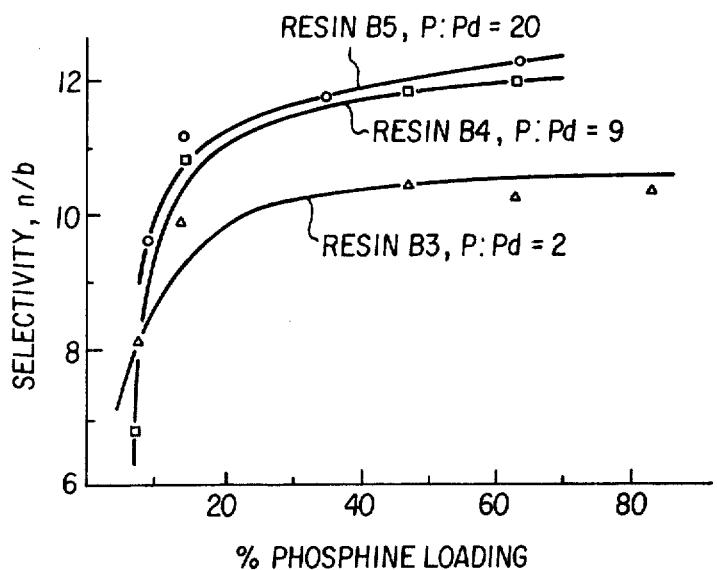
FIG. 2 describes the effects of % phosphine loading on the selectivity (n/b) of the Pd halide anchored catalyst.

FIG. 2 contains a family of curves showing how the normal:branched (n/b) selectivity varies as a function of PL, at constant P:Pd ratios, for the same series of polymer-attached catalyts shown in FIG. 1. The n/b selectivity increases rapidly as PL increases to 20 percent at all P:Pd ratios. The selectivity continues to increase as PL increases beyond 20 percent, but the rate of increase is much slower. Higher P:Pd ratios impart higher n/b selectivities.

Clearly, these results show that n/b selectivity is primarily a function of P:Pd ratio. As P:Pd ratio of a catalyst system is increased, the fraction of Ph₃P ligand about the palladium of an active catalyst complex would also be increased. This would result in a greater steric crowding about the metal, and would force the approach of the α-olefin with its terminal carbon leading to normal ester. At high PL, the phosphine concentration in a given volume within the polymer, where the catalyst is attached, would be high. This coupled with the extensive chain mobility of swellable polymers would give a higher "effective" P:Pd ratio at each metal atom than the corresponding homogeneous situation. Consequently, not only the n/b selectivity increases with increased PL, but the observed selectivity with the attached catalyst is higher than its homogeneous counterpart (e.g., n/b=11 for a resin with P:Pd=20, FIG. 2; n/b=6 for the corresponding homogeneous catalyst P:Pd=18).

Examples 75–99

These examples were carried out as in Example 48 but varying the P:Pd ratio. Examples 82–99 represent resin catalysts where P:Pd was varied at various, constant PL's. Examples 75–81 represent comparative runs carried out with homogeneous catalysts at similar P:Pd ratios.

Figure 4:
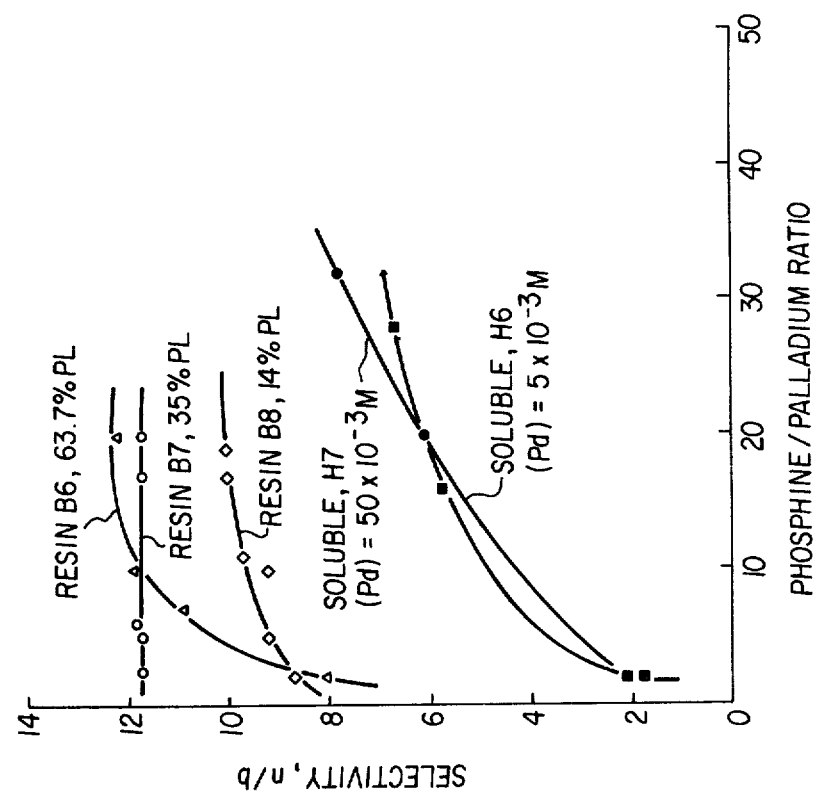
FIG. 4 describes the effects of the phosphine to palladium ratio on the selectivity (n/b) of the homogeneous and anchored catalysts.
Figure 3:
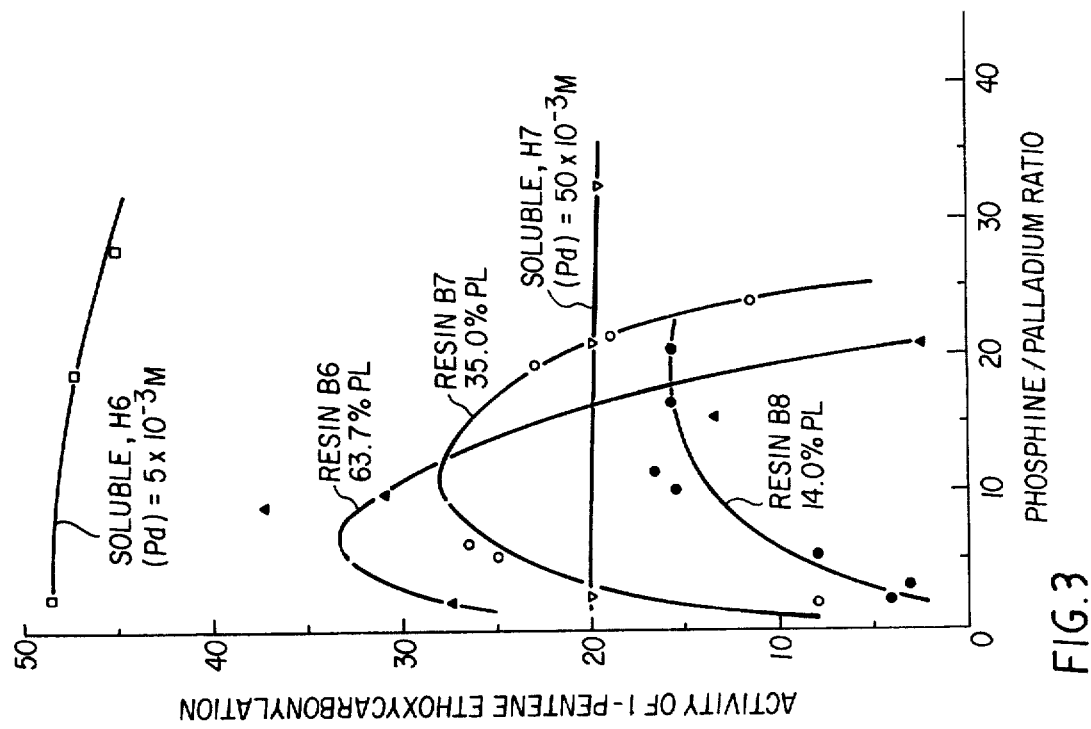
FIG. 3 describes the effect of the phosphine to palladium ratio on the activity of the homogeneous and the anchored catalysts.

Results are given in Table 4 and FIGS. 3 and 4. FIG. 3 represents the dependence of activity of the polymer on the P:Pd to ratio.

TABLE 4

| Example # | Catalyst | P:Pd | 1-Pentene Conversion (mol %)* | Selectivity (n/b) |
|---|---|---|---|---|
| 75 | Soluble, H6 | 2.0 | 48.8 | 1.9 |
| 76 | [Pd] = 5 × 10⁻³M | 16.0 | 48.7 | 5.7 |
| 77 | | 28.0 | 45.0 | 6.7 |
| 78 | | 63.0 | 41.2 | 8.1 |
| 79 | Soluble, H7 | 2.0 | 19.5 | 2.4 |
| 80 | [Pd] = 50 × 10⁻³M | 19.0 | 19.1 | 6.0 |
| 81 | | 32.0 | 18.2 | 7.7 |
| 82 | Resin, B6 | 2.0 | 27.0 | 7.8 |
| 83 | 63.7% PL | 6.9 | 37.1 | 10.8 |
| 84 | | 8.6 | 30.9 | 11.8 |
| 85 | | 14.0 | 16.5 | 11.2 |
| 86 | | 20.0 | 3.0 | 12.2 |
| 87 | Resin, B7 | 1.9 | 8.1 | 11.5 |
| 88 | 35.0% PL | 4.9 | 24.1 | 11.4 |
| 89 | | 5.6 | 26.5 | 11.8 |
| 90 | | 17.2 | 24.2 | 11.6 |
| 91 | | 20.8 | 17.5 | 11.5 |
| 92 | | 21.8 | 10.2 | 11.0 |
| 93 | Resin, B8 | 1.2 | 2.9 | 9.0 |
| 94 | 14.0% PL | 1.2 | 2.2 | 8.4 |
| 95 | | 4.1 | 7.7 | 9.2 |
| 96 | | 9.7 | 14.2 | 9.2 |
| 97 | | 15.2 | 14.4 | 9.5 |
| 98 | | 19.3 | 14.3 | 13.0 |
| 99 | | 25.0 | 9.0 | 9.9 |

*Mole % of 1-pentene conversion to ethyl hexanoate was normalized to 0.05 mmole of Pd.

The activities of the resin catalysts are more sensitive to P:Pd changes than those of the solute catalysts. Curves B6–B8 show that as the P:Pd ratios increase, at constant PL's, the activities of the resin catalysts increase to different maxima, then decrease thereafter. This is not the case with the honogeneous catalysts (curves H6 and H7). The activities of these systems decrease, even though only slightly, as P:Pd ratios increase, at constant catalyst concentrations (H6, [Pd]=5×10⁻³ M, H7, [Pd]=50×10⁻³ M). The activity of the diluted homogeneous catalyst is about two times higher than that with the concentrated catalyst (50 percent versus 20 percent conversion, after 24 hours). FIG. 3, curves B5–B8, also shows that the activity maxima exhibited by the resin catalysts move to lower P:Pd ratios as the PL's of the resins increase. Thus, resin catalysts with PL=63.7 percent, 35.0 percent, and 14.0 percent exhibited maximum activities at P:Pd=6, 10 and 14, respectively.

These observations suggest that the local phosphine concentration about a palladium metal atom exerts profound influence on the ligand dissociation and the palladium-dimer formation equilibria (Equation 5). At any given PL the catalyst's activity will be lowered at high P:Pd ratios, because fewer coordinatively unsaturated and catalytically active species exist in equilibrium. Then as P:Pd decreases, activity increases as more coordinatively unsaturated species are present. With a further decrease in P:Pd ratio, however, a second equilibria, that of the formation of palladium dimer, becomes dominant. The formation of the dimer will suppress the rate (per Pd). Thus, as observed, a maximum activity is reached, as P:Pd varies from high to low values, at the same PL. At low PL, there are fewer phosphine ligands per volume element in the resin available to retard Pd dimer formation, relative to resins having high PL, at the same P:Pd ratio. Consequently, a higher P:Pd ratio is needed at low PL than that at high PL to balance this opposing equilibria. As PL increases, more phosphines are available to a given palladium. Thus, at higher PL a lower P:Pd ratio is needed to produce the coordinatively unsaturated active catalyst complexes. This explanation, which is only hypothetical, rationalizes the observed trends shown in FIG. 3.

FIG. 3 also shows two levels of homogeneous catalyst concentration (5.0 and 50×10⁻³ M, H6 and H7, respectively) which correspond to the range of upper palladium concentration limits used within the swollen polymer beads. That is to say, the reactions are run using 0.050 mmol Pd for both the soluble and the polymer catalysts. For a total reaction volume of 10 ml, the 5.0×10⁻³ M (H6) represents the true palladium concentration in the homogeneous systems. For the case where the concentration of homogeneous catalysts is 50×10⁻³ M (H7), this corresponds more closely to the concentration of palladium found inside the polymer beads. This is the case because the average polymer volume is about 1/10 of the total solution volume. Thus, FIG. 3 also shows that when the homogeneous and attached catalysts are compared at equal palladium concentrations, the activities of some polymer catalysts are actually higher than those of the soluble catalysts (compare B6 and B7 with H7).

FIG. 4 compares the n/b selectivity for the same series of catalysts shown in FIG. 3, as a function of P:Pd ratios. In general, the polymer-attached catalysts exhibit higher selectivities than those of the homogeneous catalysts at all P:Pd ratios. For the soluble catalysts, the n/b selectivity increases with an increase in P:Pd.

For the polymer-attached catalysts, the n/b selectivity is less sensitive to P:Pd changes, except at very low P:Pd ratios (<5) where the n/b ratio increases sharply with P:Pd. The highest n/b selectivity obtained with the attached catalysts depends on the PL of the polymer. Catalysts with high phosphine loadings exhibit high n/b selectivities. Apparently, this is due to a high "effective" phosphine concentration in the vicinity of the palladium atom. This high "effective" concentration leads to a high "effective" P:Pd ratio. This special effect is quite remarkable. For example, a better than two-fold increase in n/b selectivity is obtained using resin B6 versus the homogeneous catalyst at equivalent local concentration (i.e., H7, 50×10⁻³). The selectivity is 11-12 using resin B6 (PL=64 percent) at P:Pd=10 whereas the selectivity of the homogeneous runs is only 4 to 5 at P:Pd=10.

Examples 100-131

Figure 6:
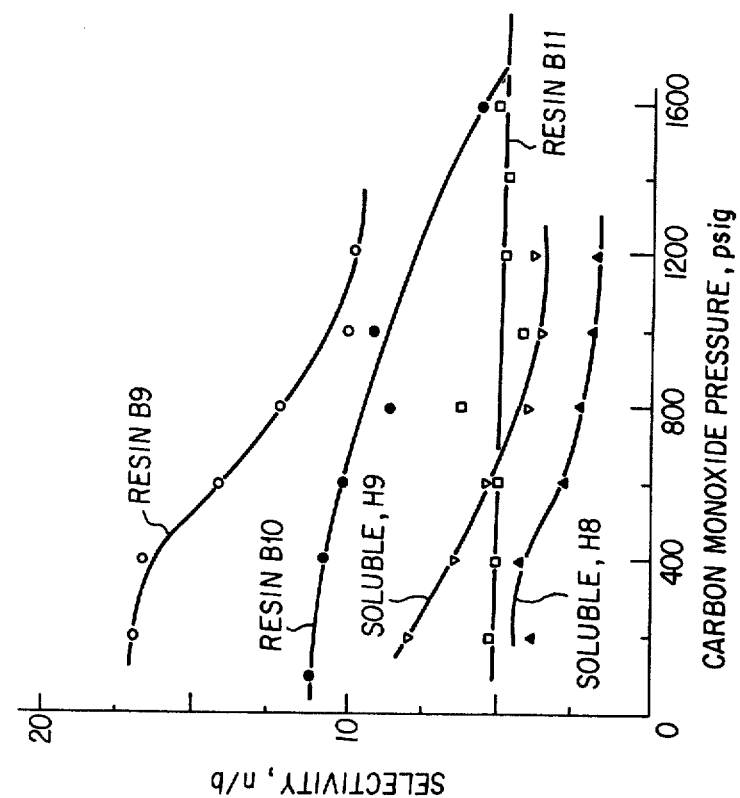
FIG. 6 describes the effect of CO pressure on the selectivity (n/b) of homogeneous and anchored catalysts.
Figure 5:
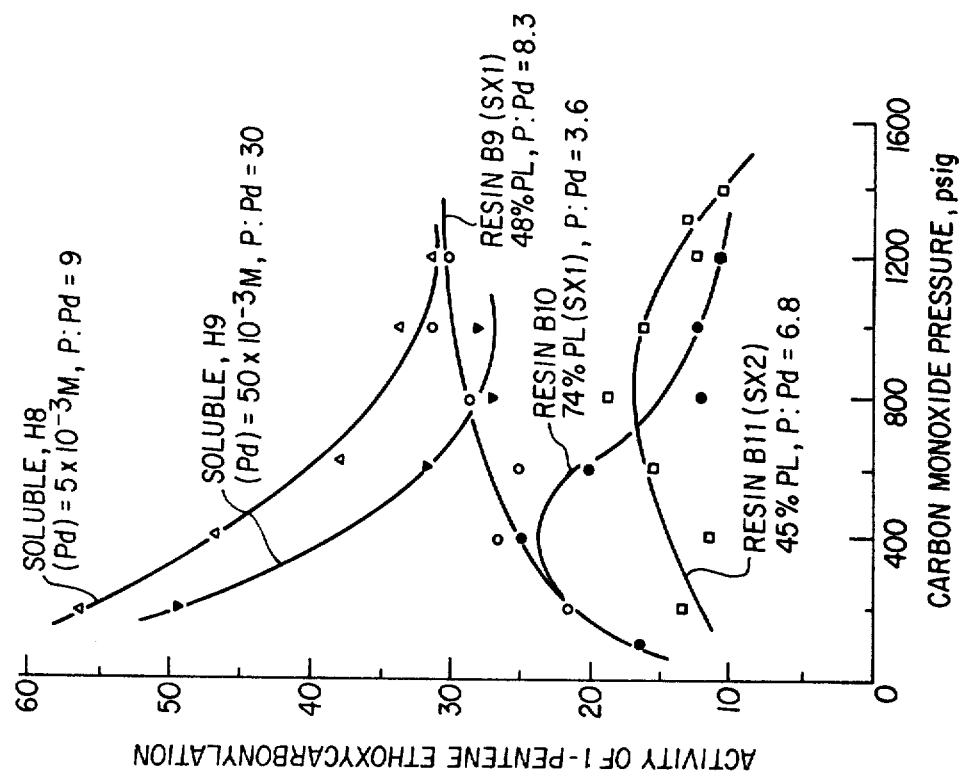
FIG. 5 describes the effects of CO pressure on the activity of homogeneous and anchored catalysts.

These examples were carried out following the procedure of Example 48 but varying the pressure of CO in the vessel. Examples 109-111 are comparative runs carried out with corresponding homogeneous catalysts. Table 5 and FIGS. 5 and 6 show the results obtained.

TABLE 5
RESULTS OF VARYING THE CARBON MONOXIDE PRESSURE ON ACTIVITY OF ALKOXYCARBONYLATION REACTION

| Example # | Catalyst | CO Pressure (psi) | 1-Pentene Conversion (mol %)* | Selectivity (n/b) |
|---|---|---|---|---|
| 100 | Soluble, H8 | 200 | 56.1 | 3.8 |
| 101 | [Pd] = 5.0 × 10⁻³M ± 5% | 400 | 51.5 | 5.2 |
| 102 | P:Pd = 9 ± 0.5 | 600 | 46.8 | 3.0 |
| 103 | | 800 | 60.3 | 2.8 |
| 104 | | 1000 | 35.7 | 1.8 |
| 105 | | 1200 | 31.0 | 1.5 |
| 106 | Soluble, H9 | 200 | 49.8 | 8.4 |
| 107 | [Pd] = 50 × 10⁻³M ± 10% | 400 | 37.2 | 6.8 |
| 108 | P:Pd = 32 ± 1 | 600 | | |
| 109 | | 800 | 26.9 | 4.7 |
| 110 | | 1000 | 28.6 | 4.8 |
| 111 | | 1400 | 31.5 | 5.0 |
| 112 | Resin, B9 | 200 | 21.7 | 16.9 |
| 113 | 48% PL (SX-1) | 400 | 26.3 | 15.5 |
| 114 | | 600 | 25.1 | 14.1 |
| 115 | | 800 | 30.2 | 12.3 |
| 116 | | 1000 | 34.8 | 10.3 |
| 117 | | 1200 | 34.8 | 10.2 |
| 118 | Resin, B10 | 100 | 16.6 | 11.4 |
| 119 | 74% PL (SX-1) | 400 | 24.9 | 12.0 |
| 120 | P:Pd = 3.6 | 600 | 20.8 | 10.6 |
| 121 | | 800 | 12.5 | 8.0 |
| 122 | | 1000 | 14.9 | 10.1 |
| 123 | | 1400 | 12.9 | 7.5 |
| 124 | Resin, B11 | 200 | 13.7 | 5.5 |
| 125 | 45% PL (SX-2) | 400 | 12.4 | 5.0 |
| 126 | P:PD = 6.8 | 600 | 15.5 | 5.2 |
| 127 | | 800 | 18.1 | 7.5 |
| 128 | | 1000 | 16.2 | 4.1 |
| 129 | | 1200 | 12.0 | 3.0 |
| 130 | | 1300 | 13.3 | 4.8 |
| 131 | | 1400 | 11.7 | 5.2 |

*Mole % 1-pentene conversion to ethyl hexanoate was normalized to 0.05 mmol of Pd.

FIG. 5 summarizes the effect of CO pressure on alkoxycarbonylation activity for both homogeneous and the polymer-attached palladium catalysts. The difference in their response to CO pressure changes is remarkable. The activity of the soluble catalysts decreases with an increase in CO pressure (catalysts H8 and H9). The activities of the polymer catalysts first increase toward maximum values as CO pressure increases in the cases of resins B10 and B11 and decrease as CO pressure is further raised. The activity increases steadily as the pressure is raised to 1200 psi for resin B9. The maximum activity attained with resin B9 (lower crosslink density polymer) is greater than those of resins B10 and B11 (higher crosslink density polymers).

These observations may be explained by the competition of CO and phosphine ligands for the vacant sites at palladium at high CO pressures. Replacement of phosphine ligands by CO causes a decrease in electron density at the metal, and this retards the rate. As CO pressure is increased, it is possible that such competition is increasingly favored in both soluble and resin catalyzed systems. However, the internal competition by phosphine for CO and the "effective" CO concentration inside the resin bead are different in the anchored systems.

FIG. 6 examines the dependence of selectivity on CO pressure. Except for resin catalyst B11, which has higher crosslink density polymer (2 percent DVB, 45 percent PL, P:Pd=7), all other resin catalysts and homogeneous catalysts show some decrease in n/b selectivity as CO pressure increases. Resin B11 shows a constant n/b selectivity of about 5 in the CO pressure range of 200-1400 psi. The decrease in n/b selectivity becomes progressively sharper with an increase in CO pressure as the crosslink densities of the resin catalysts decrease. Thus, resin catalyst B9 (1 percent DVB, 48 percent PL, P:Pd=8) has lower crosslink density and exhibits higher initial n/b selectivity (n/b=17, 200-400 psi), but drops precipitously as CO pressre is raised (n/b=10, 1200 psi). The n/b selectivity is generally lower with the homogeneous catalysts, but the decrease in n/b selectivity is about the same magnitude as catalyst B9, over the same CO pressure range of 200 to 1200 psi (63% vs. 4% decrease for catalysts H9 and B9, respectively).

Examples 132-146

These examples were carried out following the procedures of Example 48, but varying the temperature. Examples 132-136 are the corresponding runs using homogeneous catalysts as comparison. Table 6 and FIGS. 7 and 8 show the results.

Figure 7:
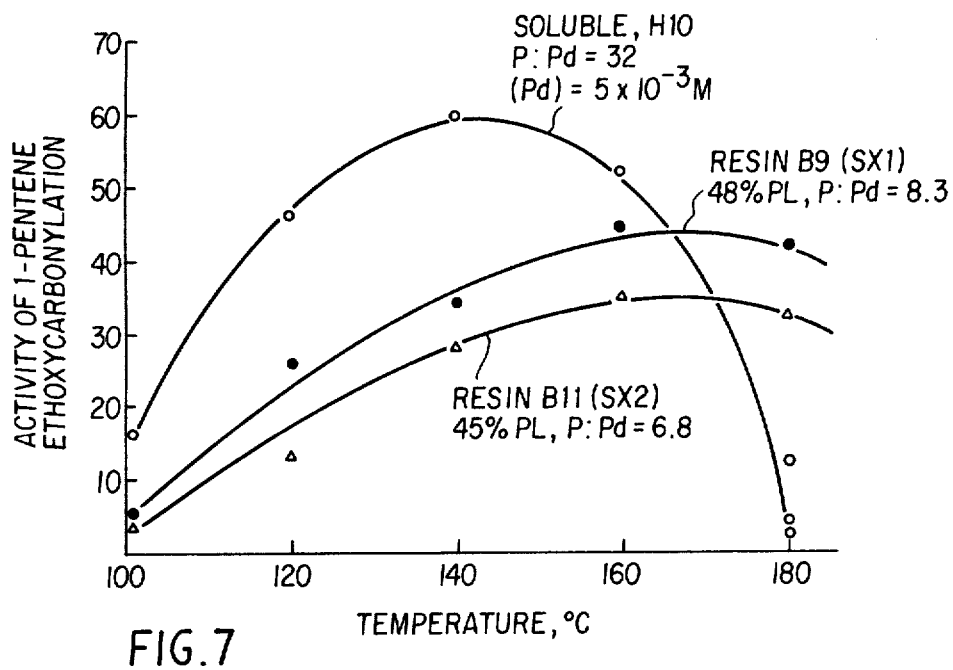
FIG. 7 describes the effect of temperature on the activity of homogeneous and anchored catalysts.
Figure 8:
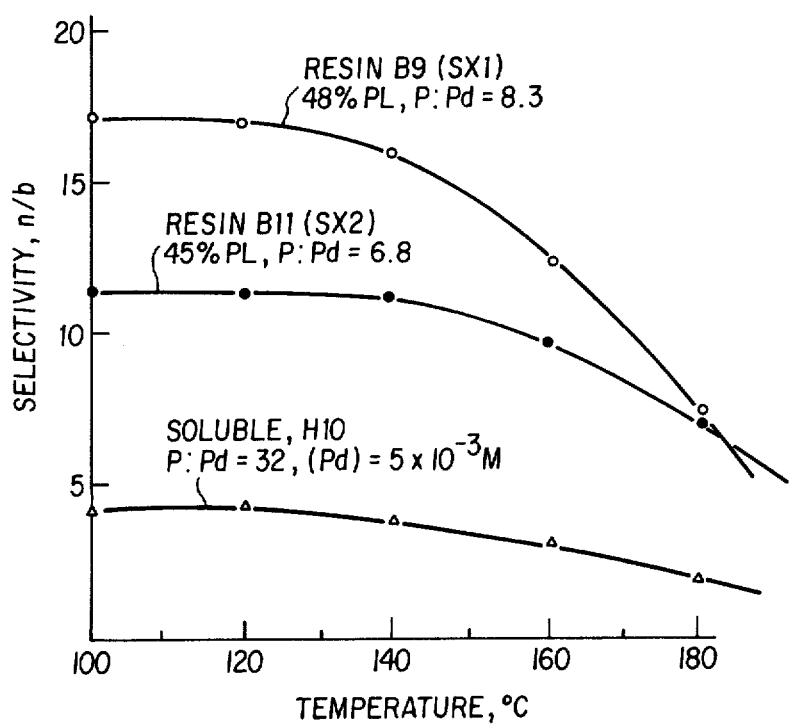
FIG. 8 describes the effect of temperature on the selectivity (n/b) of homogeneous and anchored catalysts.

FIG. 7 shows that the activity of both soluble and polymer-attached catalysts increased with temperatures until maximum activity is reached. Thereafter, further increases in temperature decrease catalyst activity. As the temperature increases, the rate of catalyst decomposition will increase. In the homogeneous solutions the rate of catalyst decomposition becomes substantial above 140°, and this leads to an overall decrease in catalytic activity. During decomposition, palladium aggregation occurs and the agglomerated material precipitates from solution while the rate decreases.

The polymer-attached catalysts are substantially more stable. Their activity continues to increase up to 160°. Apparently, the rate of the processes responsible for decomposition have been retarded in the polymer matrix. The temperature of maximum activity appears to depend on the crosslink density, the PL and P:Pd of the polymer catalysts. Resin B9, which has lower crosslink density than resin B11, shows a higher temperature of maximum activity of the two resin catalysts (about 180° versus 165°). Overall, these findings illustrate that polymer-attachment reduces the propensity of reactions which ultimately destroy the catalyst.

TABLE 6
RESULTS OF VARYING TEMPERATURE ON CATALYST ACTIVITY AND SELECTIVITY IN THE ALKOXYCARBONYLATION REACTION.

| Example # | Catalyst | Temp. | 1-Pentene Conversion (mol %)* | Selectivity (n/b) |
|---|---|---|---|---|
| 132 | Soluble, H10 | 100 | 15.8 | 4.0 |
| 133 | P:Pd = 32 ± 1 | 120 | 45.6 | 4.0 |
| 134 | [Pd] = 5 × 10⁻³M ± 5% | 140 | 60.4 | 3.8 |

TABLE 6-continued

RESULTS OF VARYING TEMPERATURE ON CATALYST ACTIVITY AND SELECTIVITY IN THE ALKOXYCARBONYLATION REACTION.

| Example # | Catalyst | Temp. | 1-Pentene Conversion (mol %)* | Selectivity (n/b) |
|---|---|---|---|---|
| 135 | | 160 | 51.8 | 3.6 |
| 136 | | 180 | 12.2 | 3.2 |
| | | | 4.6 | 3.0 |
| | | | 2.5 | 3.0 |
| 137 | Resin, B9 | 100 | 5.4 | 16.1 |
| 138 | 47.6% PL (SX-1) | 120 | 27.2 | 11.1 |
| 139 | P:Pd = 8.3 | 140 | 30.3 | 16.0 |
| 140 | | 160 | 37.8 | 12.0 |
| 141 | | 180 | 46.0 | 8.2 |
| 142 | Resin, B11 | 100 | 5.3 | 12.1 |
| 143 | 44.7% PL (SX-2) | 120 | 11.5 | 12.7 |
| 144 | P:Pd = 6.8 | 140 | 27.0 | 12.0 |
| 145 | | 160 | 34.0 | 7.7 |
| 146 | | 180 | 35.0 | 7.0 |

*Mole % 1-pentene conversion to ethyl hexanoate was normalized to 0.05 mmol of Pd.

While FIG. 7 illustrates that higher catalyst activity may be obtained at higher temperatures with the polymer-attached catalysts, FIG. 8 shows that the n/b selectivity is lower for both homogeneous and attached catalysts at high temperatures. However, the n/b selectivity is higher using the polymer-attached catalysts at all temperatures. The two polymer-attached catalysts B9 and B11 compared have about the same PL (48 percent and 45 percent) and P:Pd ratios (8 and 7) but different crosslink densities. Resin catalyst B9, which has a lower crosslink density, exhibits higher n/b selectivity than resin B11 at all temperatures. The n/b selectivity of each catalyst remains constant up to 140°. It then drops as the temperature is progressively raised.

Figure 9:
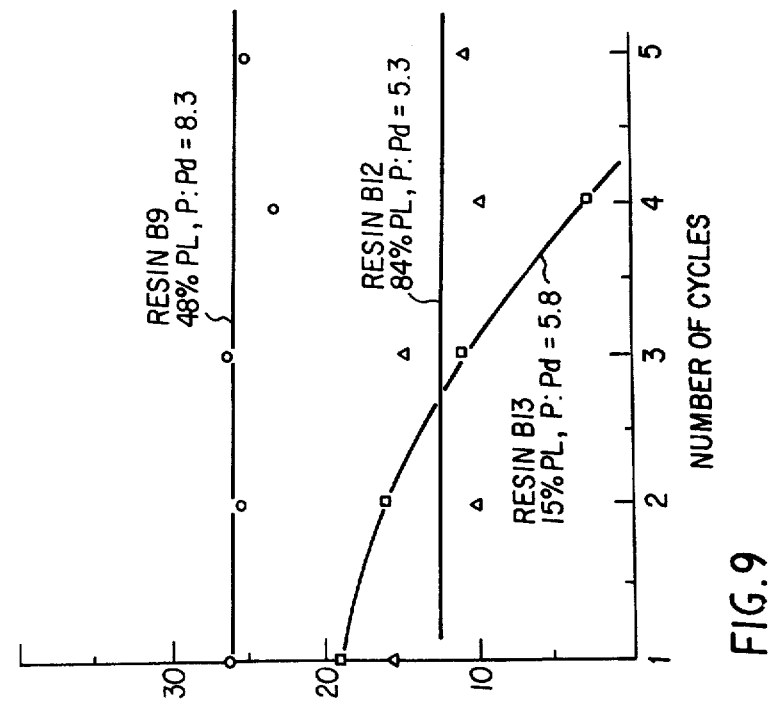
FIG. 9 describes the effect of recycle on the activity of anchored catalysts.

Examples 147–160. Activity and Selectivity Changes on Recycling Polymer-Attached Catalysts FIG. 9 shows the changes in percent conversion obtained when three polymer catalysts are recycled. The activity of the catalysts B9 (PL=48 percent, P:Pd=8.3) and B12 (PL=84 percent, P:Pd=5.3) remains unchanged after five cycles. Catalyst B13 (PL=15, P:Pd=5.8) shows a progressive decrease in activity after each cycle; its activity is almost nil after four cycles. At high phosphine loadings, the high density of the phosphine in the polymer matrix reduces catalyst dimerization and degradation reactions, as well as palladium leaching from the resin bed.

Figure 10:
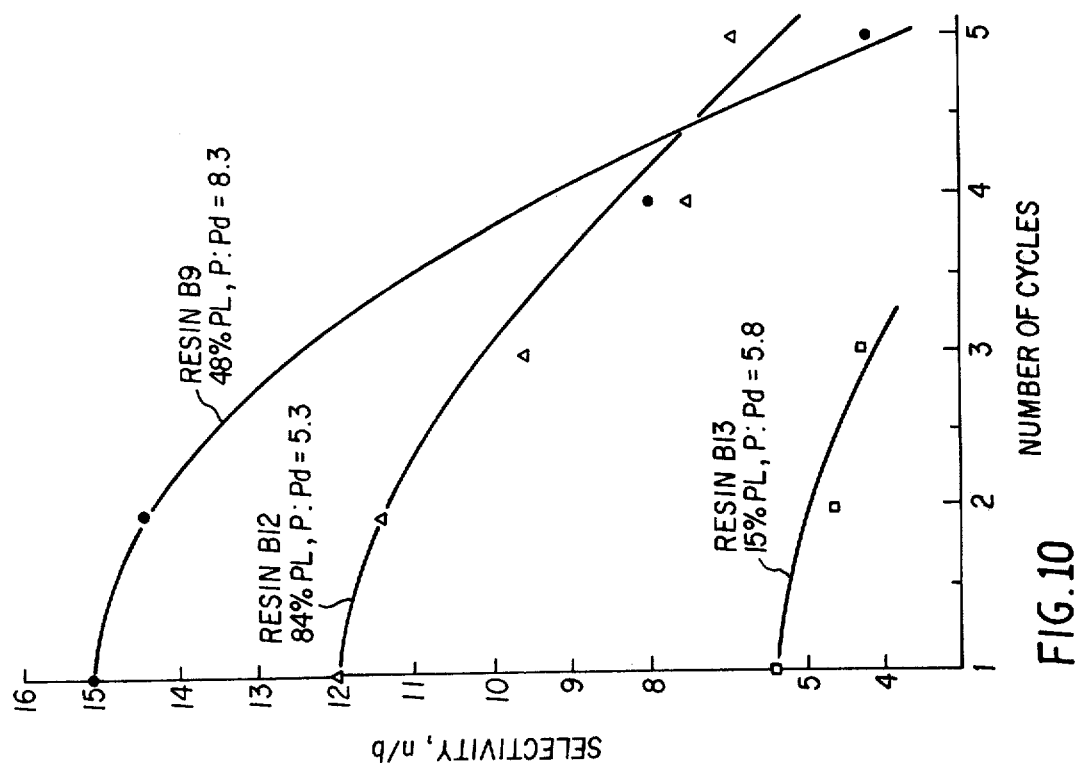
FIG. 10 describes the effect of recycle on the selectivity (n/b) of the anchored catalysts.

FIG. 10 shows that the n/b selectivity obtained with the resin catalysts (B9, B12 and B13) decreases after each cycle. The exact cause for this phenomenon is not known. However, it is possible that this is a result of the cumulative effects of phosphine oxide formation after each cycle.

Having now fully described this invention, it will be apparent to one of ordinary skill in the art that many changes and modifications can be made thereto without departing from the spirit or the scope of the invention.

What is claimed as new and intended to be covered by Letters Patent is:

1. A method for the carbonylation of α-olefins which comprises:
reacting at 70°–200° C. an olefin having 2–30 carbon atoms with carbon monoxide at a pressure of 25–2500 psi, with a primary alcohol or water, or a mixture thereof, and with a catalyst represented by the formula:

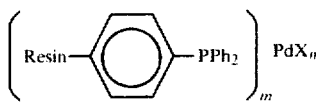

wherein
Resin-represents a non-degradable cross-linked swollen high molecular weight resin with permeatable micropores;
the sum of m and n is 4; X is a halide and wherein said α-olefin and said alcohol are capable of permeating the micropores of said swollen resin.

2. A method for the carbonylation of α-olefins which comprises:
reacting, in the absence of $SnCl_2$, at 70°–200° C. an olefin having 2–30 carbon atoms with carbon monoxide at a pressure of 25–2500 psi, with a primary alcohol or water or a mixture thereof, and with a catalyst represented by the formula

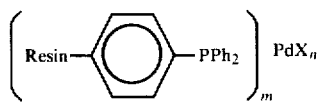

wherein
Resin-represents a non-degradable cross-linked swollen, high molecular weight resin with permeatable micropores
the sum of m and n is 4; X is a halide; and
wherein said α-olefin and said alcohol are capable of permeating the micropores of said resin.

3. The method of claim 1 or 2 wherein said carbonylation reaction is alkoxycarbonylation.

4. The method of claim 1 or 2 wherein said carbonylation reaction is hydroxycarbonylation.

5. The method of claim 1 or 2, wherein said olefin contains 2–15 carbon atoms.

6. The method of claim 1 or 2, wherein said alcohol contains 1–30 carbon atoms.

7. The method of claim 1 or 2, wherein X is chloride.

8. The method of claim 1 or 2, wherein X is bromide.

9. The method of claim 1 or 2, wherein said CO pressure is 100–1200 psi.

10. The method of claim 1 or 2, wherein said CO pressure is 400–800 psi.

11. The method of claim 1 or 2, wherein said temperature is 100°–180° C.

12. The method of claim 1 or 2, wherein said temperature is 115°–150° C.

13. The method of claim 1 or 2, wherein said reaction is carried out in the presence of a solvent capable of swelling said resin.

14. The method of claim 13, wherein said solvent is an organic solvent.

15. The method of claim 14, wherein said organic solvent is an alcohol.

16. The method of claim 13, wherein said solvent contains water.

17. The method of claim 1 or 2, wherein Resin- is 1% divinylbenzene polystyrene.

18. The method of claim 1 or 2, wherein Resin- is 2% divinylbenzene.

19. The method of claim 1 or 2, wherein the phosphine loading of said catalyst is in the range 0.5-99.5% by weight and wherein the P:Pd ratio of said catalyst is in the range 1-99.

20. The method of claim 19, wherein the phosphine loading of said catalyst is in the range 20-80%.

21. The method of claim 19, wherein the phosphine loading of said catalyst is 40-70%.

22. The method of claim 19, wherein the P:Pd ratio of said catalyst is in the range 2-60.

23. The method of claim 19, wherein the P:Pd ratio of said catalyst is in the range 5-25.

24. The method of claim 19, wherein said phosphine loading is in the range 40-70% and wherein said P:Pd ratio is in the range 5-25.

* * * * *